(12) United States Patent
Gordley

(10) Patent No.: US 7,460,235 B2
(45) Date of Patent: *Dec. 2, 2008

(54) TWO-DETECTOR GAS FILTER CORRELATION RADIOMETRY (GFCR) SYSTEM USING TWO-DIMENSIONAL ARRAY DETECTION OF DEFOCUSED IMAGE AND DETECTED-SIGNAL SUMMATION

(75) Inventor: Larry L. Gordley, Grafton, VA (US)

(73) Assignee: G&A Technical Software, Inc., Newport News, VA (US)

( * ) Notice: Subject to any disclaimer, the term of this patent is extended or adjusted under 35 U.S.C. 154(b) by 105 days.

This patent is subject to a terminal disclaimer.

(21) Appl. No.: 11/700,505

(22) Filed: Jan. 31, 2007

(65) Prior Publication Data

US 2008/0180678 A1 Jul. 31, 2008

(51) Int. Cl.
*G01N 21/00* (2006.01)
(52) U.S. Cl. .................. 356/437; 250/339.01
(58) Field of Classification Search ......... 356/432–440; 250/339.01, 339.05, 338.1, 338.5
See application file for complete search history.

(56) References Cited

U.S. PATENT DOCUMENTS

| 4,578,762 | A * | 3/1986 | Wong ........................... 702/32 |
| 5,128,797 | A * | 7/1992 | Sachse et al. ............... 359/246 |
| 6,294,785 | B1 * | 9/2001 | Gordley .................. 250/339.09 |
| 6,853,452 | B1 * | 2/2005 | Laufer ......................... 356/436 |
| 6,900,893 | B2 * | 5/2005 | Foley et al. ................. 356/437 |
| 2006/0139648 | A1 * | 6/2006 | Sachse et al. ............... 356/437 |

* cited by examiner

*Primary Examiner*—Hoa Q Pham
(74) *Attorney, Agent, or Firm*—Peter J. Van Bergen

(57) ABSTRACT

A GFCR system receives light from a scene of interest and focuses it to form an image. Light associated with a selected field-of-view of the image is confined to a spectral band absorbable by a gas of interest and is split into first and second paths. A region that does not substantially interfere with the spectral band is disposed in the first path. A first two-dimensional array of optical detection elements is disposed in the region along with a first diffuser. Disposed in the second path are a gas cell filled with the gas of interest, a second two-dimensional array of optical detection elements, and a second diffuser. The first and second optical arrays generate output signals that are summed to form corresponding first and second sums. A difference between the first and second sums is generated and normalized as a direct measure of the gas of interest.

17 Claims, 5 Drawing Sheets

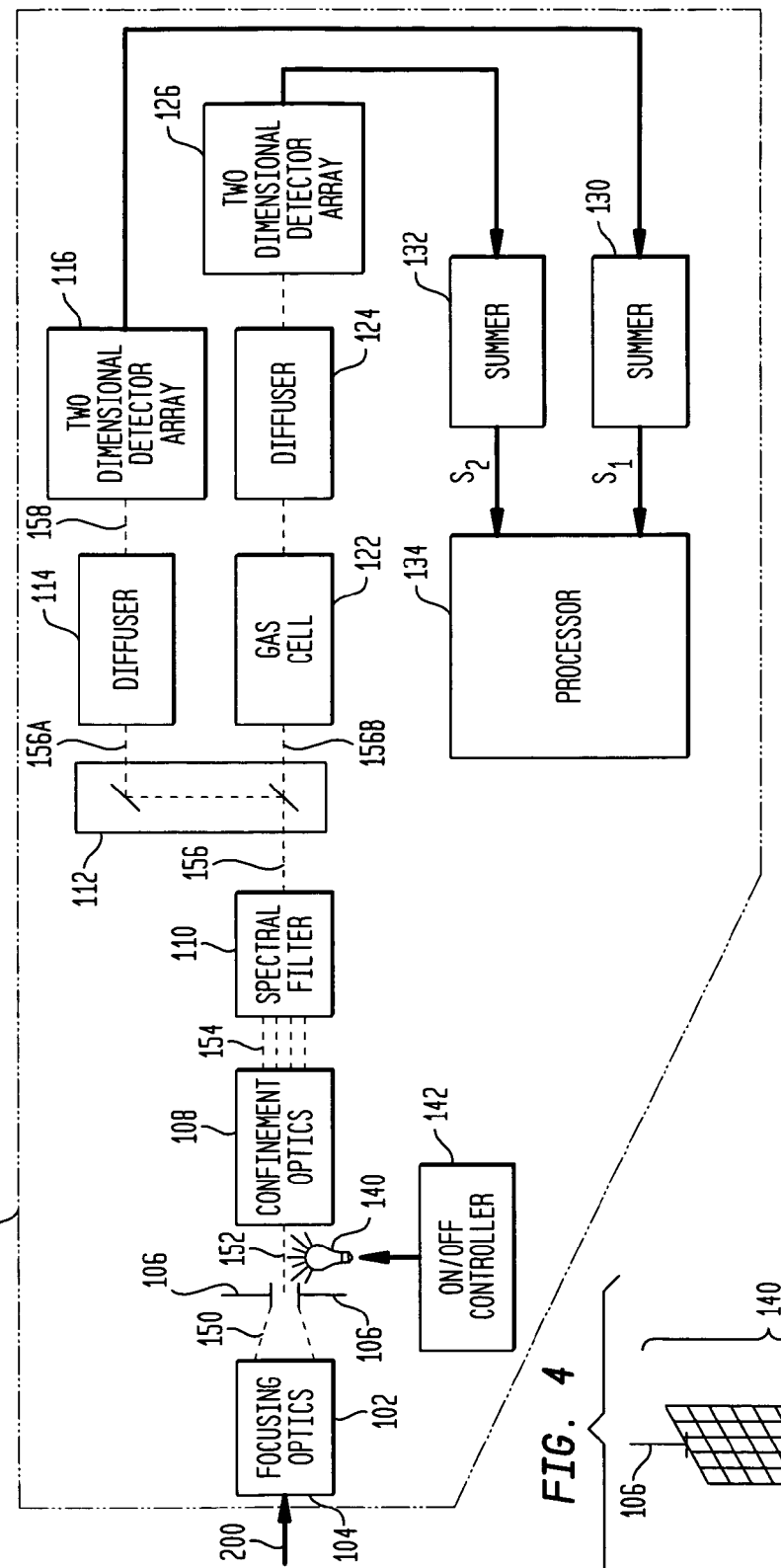

TWO-DETECTOR GAS FILTER CORRELATION RADIOMETRY (GFCR) SYSTEM USING TWO-DIMENSIONAL ARRAY DETECTION OF DEFOCUSED IMAGE AND DETECTED-SIGNAL SUMMATION

CROSS-REFERENCE TO RELATED PATENT APPLICATIONS

This patent application is co-pending with one related patent application entitled "INTERNALLY-CALIBRATED, TWO-DETECTOR GAS FILTER CORRELATION RADIOMETRY (GFCR) SYSTEM", filed by the same inventor and owned by the same assignee as this patent application.

FIELD OF THE INVENTION

The invention relates generally to gas filter correlation radiometry (GFCR), and more particularly to a two-detector GFCR system that detects a defocused image using two-dimensional arrays with the signal outputs from each array being summed and then processed to provide a measure of a target gas in the GFCR system's line-of-sight.

BACKGROUND OF THE INVENTION

"Gas filter correlation radiometry" (GFCR) is an optical remote sensing method used to produce highly sensitive measurements of "targeted" gases. A conventional GFCR measurement system using two single-element detectors is shown in FIG. 1 and is referenced generally by numeral 10. The basic elements of GFCR system 10 form an optical train that includes:

focusing optics (e.g., a telescope) 12 that focuses the image contained in light 200 onto a field stop 14 that sets the field-of-view of the light focused by optics 12, optics 16 that collimate the light passing through field stop 14, a chopper 18 used to modulate the collimated light, a spectral filter 20 that confines the light (collimated by optics 16) to a specific spectral bandpass where (spectrally) a gas of interest absorbs, optics 22 for splitting the spectrally filtered light into two paths 24 and 26 where path 24 defines a region that is non-absorbing within the spectral bandpass at which the gas of interest absorbs, a single-element, light-intensity detector 28 disposed in path 24, and a gas cell 30 filled with a gas of interest (i.e., the target gas) and disposed in path 26 such that the light traveling thereal-ong passes through gas cell 30 prior to impinging on a single-element, light-intensity detector 32.

GFCR system 10 further uses "back-end" electrical components that includes balancing electronics 40 coupled to the outputs of detectors 28 and 32. In general, balancing electronics 40 include a balancing amplifier 42, a differential amplifier 44 and a gain amplifier 46 that cooperate to measure a difference between the outputs of detectors 28 and 32.

GFCR system 10 uses a sample of the gas to be detected (i.e., the target gas) as a filter for removing sensitivity to that gas in path 26. That is, the light is passed through field stop 14, collimated, and spectrally filtered with broadband filter 20 to confine the light to a spectral bandpass where the target gas absorbs. After the beam is split by optics 22, gas cell 30 absorbs light from spectral wavelengths coinciding with spectral absorption features (i.e., typically spectral absorption lines) of the target gas.

In practice, the detector signals from detectors 28 and 32 are electronically balanced to be approximately equal when viewing light 200 from an unattenuated light source such as the sun observed above the atmosphere from a satellite. Then, when the light source is observed through the atmosphere during solar occultation, a difference between the two signals is induced and measured. Absorption by the target gas in the observed scene attenuates the vacuum path signal generated by detector 28. However, the gas path signal generated by detector 32 is minimally attenuated. The difference signal (i.e., the difference between the two signals generated by detectors 28 and 32) is highly sensitive to and correlated with the amount of target gas in the line-of-sight of GFCR system 10.

Useful GFCR measurements must be tailored to the absorption characteristics of the target gas, and depend on the ability to maintain a stable and calibrated gas cell containing a sample of the target gas. For example, when the GFCR method was employed in a solar occultation experiment (i.e., the "halogen occultation experiment" or HALOE), sensitivities of $10^{-5}$ in mean band absorption were achieved by a system similar to that depicted in FIG. 1. The two detectors' signals were differenced and balanced by electronics 40 to give nearly zero difference during solar observation above the atmosphere. The difference signals measured during solar occultation were used very successfully as measures of target gas absorption. To achieve high precision, the difference signals included an additional gain of one hundred or more. The key to making these measurements is the ability to determine the balance and rate of change of the difference signal immediately before the observation, which mitigates error due to drifts in detector response. To achieve the desired measurement accuracy of 1 part in $10^5$, the balance must be known to $10^{-5}$ of the full broadband signal. Thus, small drifts in detector response, if not detected and corrected, can severely corrupt the difference measurement.

In addition to use in solar occultation, there has been hope that GFCR could be used for solar backscatter measurements, which could yield much better geographical coverage than solar occultation and be realized using small commercial devices. However, because the conventional two-detector method requires continuous high-precision calibration of the balance condition (i.e. calibration of the signal drift due to changes in system response), most researchers have abandoned the two-detector method in favor of single-detector methods. Unfortunately, while single-detector methods can nearly eliminate detector instability as an error source by measuring both signals with the same detector, they introduce a host of other problems, depending on method of implementation. For example, if the gas cell condition is modulated by changing pressure or optical mass, there is a significant decrease in sensitivity because the cell modulation produces a relatively small spectral difference between paths. The signals are also difficult to model because of gas heating and cell state variation that may not reach uniform equilibrium.

In another single-detector method, the light path is switched between a gas-cell path and a non-gas-cell (e.g., vacuum) path by either rapidly re-routing the beam (e.g., polarization switching techniques) or moving the gas cell into and out of the beam. However, both of these approaches introduce noise due to beam steering and loss of signal integration time due to time between modulated states.

An even greater problem with any single-detector method is the loss of measurement simultaneity and/or the ability to exactly match field-of-views for gas and vacuum paths. If the scene changes during the time necessary to switch between modulated states or because of field-of-view mismatch, the change in normalized difference signal (caused by scene brightness variation) will corrupt the data interpretation that assumes the difference signal is produced solely by spectral variation. For example, a satellite traveling at 7 km/sec encountering a 1% per kilometer change in mean scattering brightness over the field-of-view will experience a fractional brightness change of $10^{-4}$ in 1.4 milliseconds which would be falsely interpreted as spectral variation. This presents a severe problem for the single-detector method, or any method that does not make simultaneous and spatially identical measurements of the two states (i.e., gas path and vacuum path).

SUMMARY OF THE INVENTION

Accordingly, it is an object of the present invention to provide a GFCR system.

Another object of the present invention is to provide a GFCR system that employs a two-detector methodology.

Still another object of the present invention is to provide a GFCR system using simultaneous light-absorbing and non-light-absorbing path detection that does not require the use of back-end electrical components to balance the system.

Other objects and advantages of the present invention will become more obvious hereinafter in the specification and drawings.

In accordance with the present invention, a gas filter correlation radiometry (GFCR) system includes an optical train that receives light from a scene of interest at an entrance aperture. The light is focused to form an image of the scene at a focal plane within the optical train. The optical train confines light from a selected field-of-view of the image at the focal plane to a spectral band at which a gas of interest absorbs. The optical train splits the confined light into first and second paths. A region that is substantially non-interfering with respect to the spectral band is disposed in the first path. A first optical detector defined by a two-dimensional array of optical detection elements is disposed in the region. A first diffuser is also disposed in the region at a position that is optically in front of the first optical detector. The first diffuser assures that each portion the light from the selected field-of-view of the image is identically distributed across at least a portion of the optical detection elements of the first optical detector. A gas cell filled with the gas of interest, a second optical detector defined by a two-dimensional array of optical detection elements, and a second diffuser are disposed in the second path. The collimated light passed through the gas cell impinges on the second diffuser at a position that is optically in front of the second optical detector. The second diffuser assures that each portion of the light from the selected field-of-view of the image is identically distributed across at least a portion of the optical detection elements of the second optical detector. Each optical detection element of the first and second optical detectors generates an output signal. The output signals are summed to form corresponding first and second sums. A difference between the first and second sums is generated and normalized as a direct measure of the gas of interest.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein:

FIG. 3 is a schematic view of the GFCR system in FIG. 2 further equipped with an internally-mounted light producer that can be used to continuously calibrate the GFCR system;

FIG. 4 is a schematic view of the front end of the GFCR system in FIG. 3 further illustrating an embodiment of the light producer;

DETAILED DESCRIPTION OF THE INVENTION

The present invention is a gas filter correlation radiometry (GFCR) system utilizing a two-detector methodology to simultaneously provide light-absorbing and non-light absorbing measurements without requiring any back-end electronics to balance the system. The system structure also provides for novel approaches to on-board balance calibration and data analysis calibration.

Figure 2:
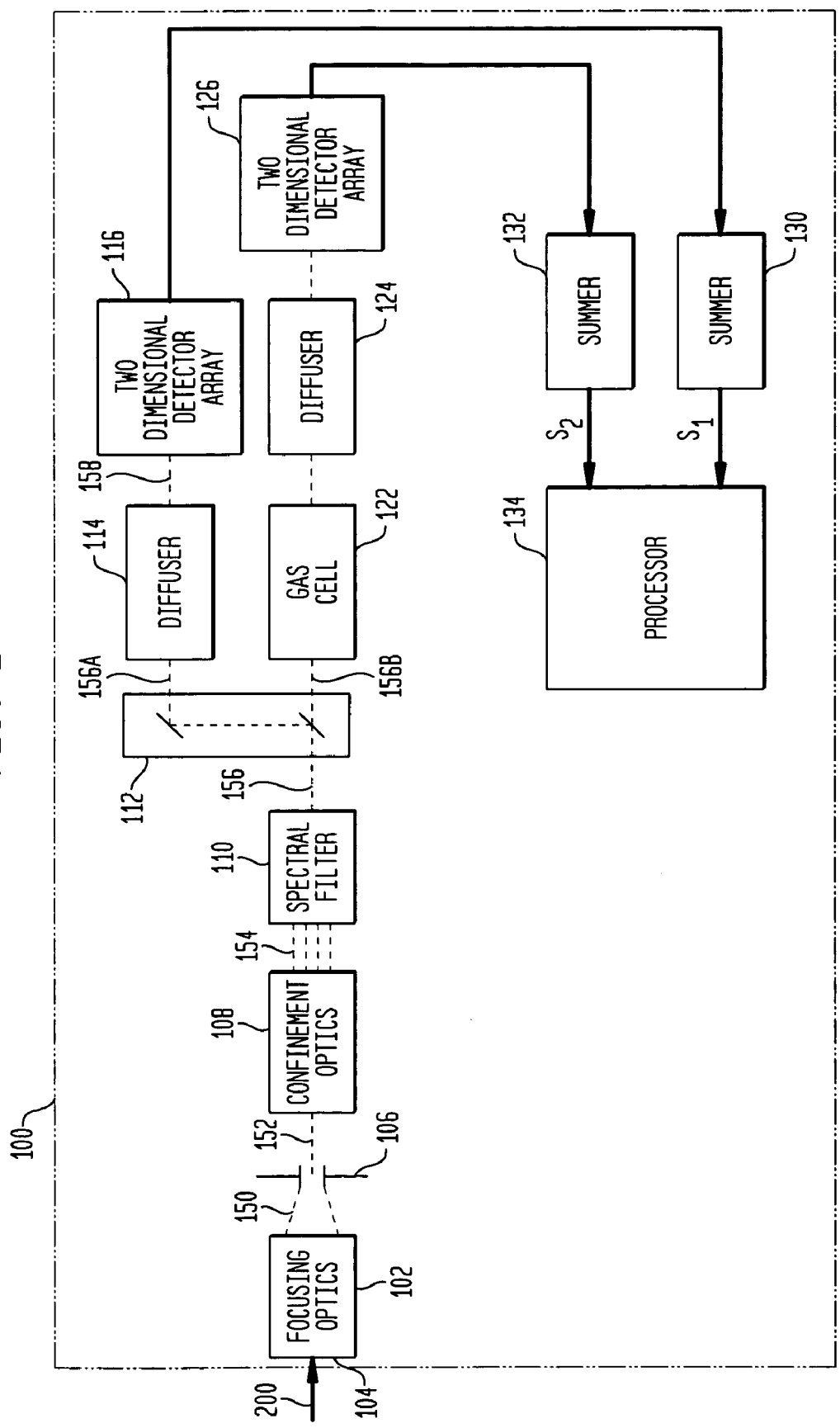
FIG. 2 is a schematic view of a GFCR system that produces a defocused beam and detects same using two-dimensional arrays with the signal outputs from each array being summed and then processed to provide a measure of a target gas in accordance with the present invention.

Referring again to the drawings and more particularly to FIG. 2, a GFCR system in accordance with an embodiment of the present invention is shown and is contained within the dashed-line box referenced by numeral 100. In GFCR system 100, optical signal transmission between elements thereof is indicated by dashed-lines and electrical signal transmission between elements thereof is indicated by solid lines that terminate in an arrowhead.

GFCR system 100 provides a measurement of a gas of interest or "target gas" by processing an external scene light 200 that defines a scene being imaged some distance away from GFCR system 100. At the optical "front end" of GFCR system 100, focusing optics 102 define an entrance aperture 104 of GFCR system 100. Focusing optics 102 operate to focus light 200 impinging on entrance aperture 104 onto a plane where a field stop 106 is positioned. That is, an image defined by scene light 200 received at entrance aperture 104 is focused at field stop 106. The image so-focused is referenced by numeral 150. The particular choice and arrangement of elements used to construct focusing optics 102 can be achieved by a variety of embodiments. Accordingly, it is to be understood that the particular choice of elements comprising focusing optics 102 is not a limitation of the present invention.

Field stop 106 defines a selected field-of-view of focused image 150 with the selected image 152 being transmitted to confinement optics 108. As would be understood in the art, confinement optics 108 is any one or more optical elements that keep light (from selected image 152) from diverging outside the optical boundaries of GFCR system 100. In many instances, confinement optics 108 is realized by one or more optical elements that "collimate" or nearly collimate the light of interest (i.e., the light associated with image 152) in order to efficiently transfer the light along an intended optical path. Accordingly, the output of confinement optics 108 typically produces collimated light as indicated by dashed lines 154. However, it is to be understood that there may be implementations of the present invention that are optically "short" such that beam divergence is minimal in which case collimating optics may not be required.

A spectral filter 110 disposed in the path of collimated light 154 passes a specific spectral band of collimated light 154 that is referenced by dashed line 156. The spectral band will include the wavelength(s) that would be absorbed in the presence of the target gas of interest.

The spectral band passed by spectral filter 110 impinges on beam splitting optics 112 (e.g., beam splitter, mirror, etc.) where light 156 is split and transmitted as two spatially-separated and nearly identical light beams 156A and 156B for further processing. Light 156A travels along a path that will not cause absorption (or significant attenuation or spectral interference) of any wavelength(s) of light that would be absorbed by the target gas of interest. To exhibit such "non-absorbing" characteristics, the path along which light 156A travels can be defined by a media or region that achieves this result. Accordingly, the region along which light 156A travels could be evacuated, filled with a gaseous media that is non-absorbing, or contain a solid material that is transparent or nearly transparent to the spectral band of light 156A and non-absorbing with respect to wavelength(s) of light that can be absorbed by the target gas of interest. The method/structure used to achieve the non-absorbing characteristics of the path traveled by light 156A is not a limitation of the present invention.

Disposed in the path of light 156A are a diffuser 114 and a two-dimensional array of optical (e.g., light) detection elements or "two-dimensional detector array" 116 as it will be referred to herein. Detector array 116 is any high-density, two-dimensional array of elements where each element can detect light and generate an electrical signal that corresponds to the light's intensity. Such detector arrays are available commercially from a variety of vendors. The choice of detector array typically depends on many factors to include, for example, spectral response, sensitivity, and other specific application details that are not pertinent to or limitations of the present invention. Also, the particular size of the array (i.e., number of pixels), the array's frame (read-out) rate, and other specifications are not limitations of the present invention.

Diffuser 114, which is positioned optically ahead of detector array 116, represents optical elements that cooperate with preceding optical elements in GFCR system 100 to diffuse or defocus image 152. More specifically, each portion or point of image 152 at the field-of-view (FOV) of field stop 106 is identically distributed (as referenced by dashed line 158) as it impinges across some or all of the light detection elements of detector array 116. That is, diffuser 114 represents any optical element(s) needed to assure that each portion or point of light in image 152 at field stop 106 is spread or smeared over detector array 116 in the same proportion as any other point of light in the same image. In this way, detector array 116 senses a change in light from the scene (i.e., a change in external scene light 200) with effectively a constant ensemble response regardless of which portion of the scene changed.

By way of a non-limiting example, diffuser 114 can assure this identical distribution (or defocus) of image 152 (at the FOV of field stop 106) by creating an image of entrance aperture 104 on the image plane of detector array 116 that is defined by the light detection elements thereof. This can be explained as follows. Light emanating from a point at field stop 106 that is traced back through focusing optics 102 will induce a uniform or even distribution of light intensity across entrance aperture 104. This is also true for the sum of all points in the plane of field stop 106. Therefore, by taking the image emanating from field stop 106 (i.e., image 152) and using it to create an image of entrance aperture 104 at the image plane of detector array 116, light from each point at field stop 106 will be more uniformly or evenly distributed across the image plane of detector array 116. In effect, this creates a totally defocused far-field image. Thus, a change in light intensity emanating from any point in the FOV of field stop 106 will induce a change that is identical to a similar intensity change experienced by any other point in the FOV. This nearly eliminates the problem of false difference signals between detectors caused by non-uniform detector response for the detector elements (or non-uniform detector surface response for single-element detectors).

Disposed in the path of the light 156B are a gas cell 122, a diffuser 124, and a two-dimensional array of optical (i.e., light) detection elements referred to as two-dimensional detector array 126 that is similar to detector array 116. While detector arrays 116 and 126 are shown as physically distinct elements, the present invention is not so limited. That is, the function of detector arrays 116 and 126 could also be realized using a single two-dimensional detector array having independently accessible and addressable detector areas that could simultaneously and independently receive/process two distinct beams of light.

Figure 1:
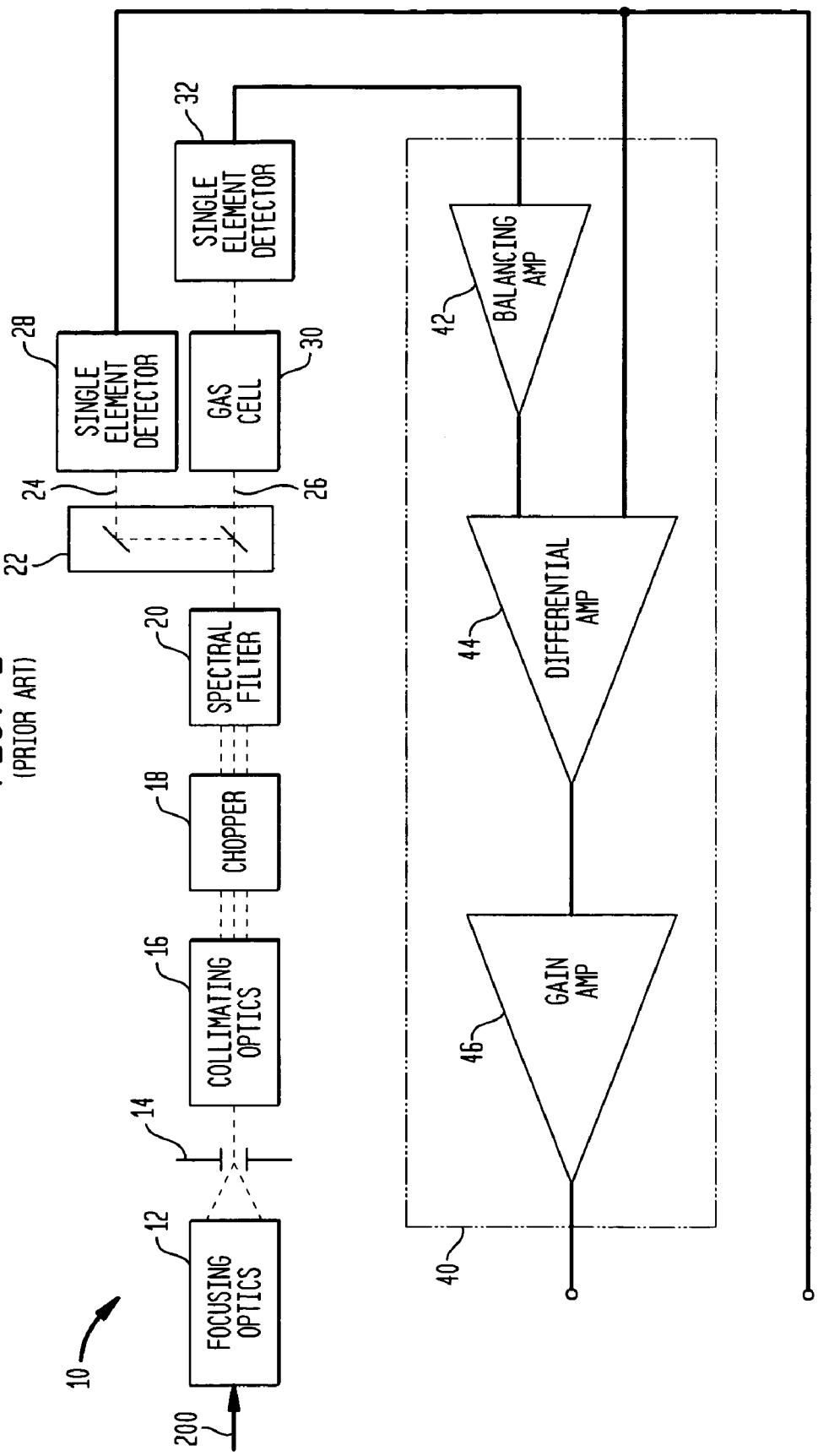
FIG. 1 is a schematic view of a conventional gas filter correlation radiometry (GFCR) system employing two single-element detectors and back-end electronics used to balance the system.

Gas cell 122 performs the same function as gas cell 30 (FIG. 1) used in conventional GFCR systems. That is, gas cell 30 is filled with the target gas that will absorb light at wavelength(s) passed by spectral filter 110. The resulting light passed by gas cell 122 is transmitted to diffuser 124 that functions in the same way as diffuser 114. Accordingly, diffuser 124 cooperates with the preceding optical elements in GFCR system 100 to diffuse or defocus image 152 in a way that causes it to be evenly distributed as it impinges across some or all of the light detection elements of detector array 126. Similar to diffuser 114, diffuser 124 can assure this even distribution of the image by creating an image of entrance aperture 104 on the image plane of detector array 126 as described above for diffuser 114/detector array 116.

The individual light detection element outputs from each of detector arrays 116 and 126 are electrical signal representations of the detected light intensity. These electrical signals are processed directly to generate a measure of the target gas of interest present in the scene represented by light 200. Processing of these electrical signal outputs can be achieved by a variety of hardware configurations without departing from the scope of the present invention. For example, the processing can be achieved by a single processor or multiple processors. Accordingly, it is to be understood that the separate functional blocks used to represent the processing structure in FIG. 2 are used simply to facilitate a description of the present invention.

The outputs from detector array 116 are summed at a summer 130 to generate a signal $S_1$, and the outputs from detector array 126 are summed at a summer 132 to generate a signal $S_2$. The sum signals $S_1$ and $S_2$ are used by a processor 134 to generate a measure of the target gas of interest present in the scene represented by light 200. In general, processor 134 calculates a normalized difference using signals $S_1$ and $S_2$. More specifically, processor 134 generates a difference between $S_1$ and $S_2$, and normalizes (i.e., divides) this difference using $S_1$, $S_2$, or the sum of $S_1$ and $S_2$. The normalized difference is directly dependent on the light absorption difference between the two signals, but is independent of the light intensity.

The advantages of the present invention are numerous. The present invention creates a totally defocused image, detects the defocused image using a two-dimensional detector array, and requires only simple signal summation and subsequent difference signal processing for a two-detector GFCR method. This GFCR system eliminates the problems associated with the conventional two-detector GFCR system that requires sensitive back-end difference signal balance and gain electronics. As a result, the GFCR system of the present invention provides a novel and robust approach to GFCR.

By detecting a defocused beam using tens to thousands of rapid read-out pixels from high-density detector arrays, the sum of the pixel readings generated in the present invention serves as a very high-precision and direct measure of the beam intensity. For example, the HAWAII detector array series by Teledyne Imaging Sensors, with array sizes of 1000×1000 (i.e., $10^6$ pixels), can be read at KHz ($10^3$/sec) frame rates with well depths of $10^5$ electrons, and per-pixel read-out noise under 100 electrons. This allows counts of up to $10^5 \times 10^3 \times 10^5 = 10^{14}$ electrons in one second of integration time, yielding potential signal-to-noise limits of the square root of the counts or $10^7$. A typical approach would sum pixel outputs by right shifting digital values as needed during the summation process to limit the final sum to the desired digital word size (e.g., 32 bits allows integers of $4.3 \times 10^9$).

The present invention also improves detection linearity since light being measured can be spread over a relatively large surface area to reduce irradiance (flux power/area). Surface response uniformity of the detector array is far superior to single-element detectors to thereby further enhance the defocusing effect. By using detector arrays, the effect can be enhanced further by well know "flat-fielding" procedures that mathematically correct the output to the equivalent of a detector array system with perfectly uniform response. This nearly eliminates false difference signals due to scene irregularity that can correlate with detector surface response irregularity. In summary, the GFCR's defocusing aspects are fully exploited by the present invention's novel use of two-dimensional detector arrays.

The present invention also exhibits the advantageous measurement characteristics of spatial and temporal simultaneity where exactly the same scene is measured at exactly the same time. This eliminates the systemic scene variation error inherent in modulated single-detector systems.

The above-described GFCR system can be further enhanced by providing an on-board calibration system. Referring now to FIG. 3, a GFCR system 300 includes all of the elements of GFCR system 100 which are referenced using the same reference numerals. In addition, GFCR system 300 has an internally-mounted calibration light producer. In general, a portion of the internally-generated light will traverse the same path as external scene light 200. That is, the portion of the internally-generated light that travels the same path as the scene light is confined/collimated, spectrally filtered, split, and ultimately distributed over the imaging plane of detector arrays 116 and 126 similar to the way that external scene light 200 is processed and distributed over detector arrays 116 and 126. In addition, the difference in distribution can be calibrated and mathematically corrected during data processing to produce a nearly perfect distributional match and superior calibration signal. This correction process includes ignoring the output signals generated by "pixels" that do not receive scene light. In effect, this allows the calibration procedure to reject any part of the calibrating light that does not traverse the same path as the scene light.

The purpose of the calibration light producer is to create light that appears to emanate from within the scene image at field stop 106. This could be done in a variety of ways. For example, light emitting elements (not shown) could be placed within the aperture of field stop 106 or, as depicted by way of example in FIGS. 3 an 4, a light producer 140 could be used that illuminates scattering elements (not shown in FIG. 3 to maintain clarity in the illustration) placed within the aperture of field stop 106. Since the light generated by light producer 140 is generally dispersed over a wide angle relative to the scene light passing through field stop 106, only a portion of the calibrating light from light producer 140 will traverse the same path as the scene light. The portion of the calibration light that traverses the same path as external scene light 200 falls on the detector arrays in a nearly identical distribution over the detector elements (pixels) used to image GFCR system aperture 104. As described above, the analysis discards signals from other pixels.

The signal from the calibration light can be distinguished from the scene light by blocking the scene light when the calibration light is on, or simply measuring the difference in signals between states of light-on and light-off. The calibration signal becomes a measure of a false difference signal produced by the drift in system response. This is equivalent to the signal that would be observed by looking at an external unattenuated light source. In this way, GFCR system 300 includes the means to accurately and precisely estimate the change in detector array response with the confidence that each detector array is being used for calibration in exactly the same proportion as would be the case for external scene light 200. The use of detector arrays makes it mathematically possible to correct for residual differences in illumination uniformity of the scene light vs. the calibration light, which is a major improvement in calibration capability.

For continuous calibration capability, it typically will be desirable to turn light producer 140 on and off in accordance with a known sequence (e.g., a periodic blinking sequence). Accordingly, an on/off controller 142 can be coupled to light producer 140. The "on" portion of the sequence will generate light that is used to create summed calibration signals from summers 130 and 132, with the summed calibration signals then being used to generate a normalized difference as was done for light 200.

When GFCR system 300 is in the calibration mode (i.e., light producer 140 is on), external scene light 200 can continue to be present or can be blocked. In either case, it is the change in output signal (when light producer 140 is on vs. when it is off) that is used to calibrate the system. For the best measurement precision, it is preferable to block light 200 during the time that light producer 140 is on so that a constant offset is attained. This means that GFCR system 300 must be equipped with some means (not shown) to block light 200 when in the calibration mode. If such light blocking means is not available or practical, calibration can still be achieved in the presence of both light 200 and light from light producer 140. In such a case, calibration must be performed when light 200 is not "noisy" or by statistical processing to determine the change in the output signal when light producer 140 is on.

A variety of embodiments of light producer 140 can be employed without departing from the scope of the present invention. For example, as illustrated in FIG. 4, light producer 140 can be achieved by mounting a grid element 140A in the aperture of field stop 106, and providing a light source 140B at a position that is optically behind grid element 140A with respect to entrance aperture 104. When light source 140B is turned on by controller 142, the light therefrom is scattered by grid element 140A with the scattered light then being defused across the image plane of the detector array as previously described.

Optimum use of the calibration signal requires that the calibration beam distribution on the detector array be well matched to the scene beam distribution on the detector array. Such matching can be achieved optically or can be achieved mathematically during data processing provided individual "pixel" values of the detector array can be measured/read.

Figure 5:
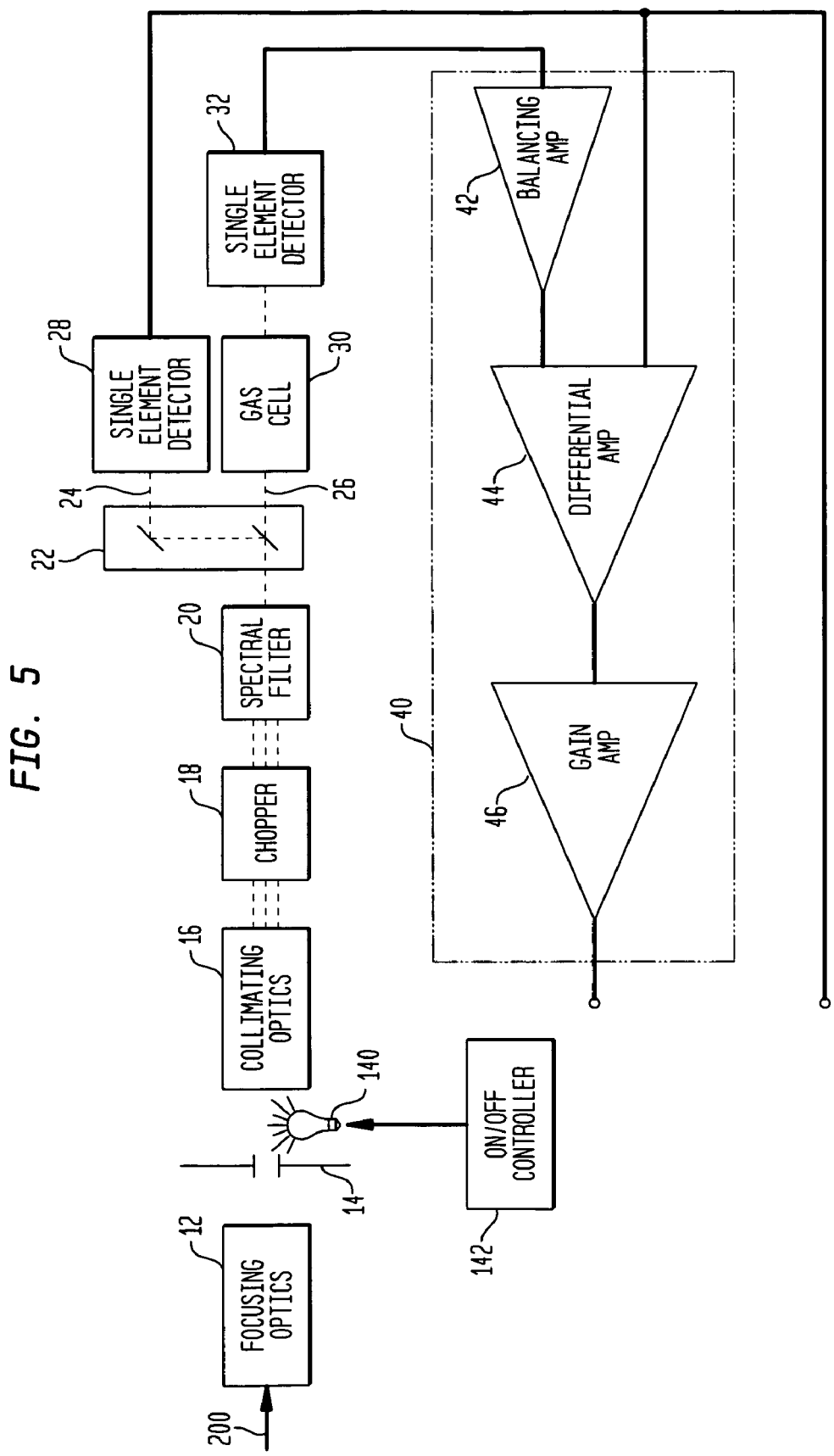
FIG. 5 is a schematic view of the conventional GFCR system employing two single-element detectors that is further equipped with an internally-mounted light producer that can be used to continuously calibrate the GFCR system.

The advantages of using light producer 140 are not limited to the use thereof in the present invention's novel GFCR system. That is, light producer 140 and controller 142 could be incorporated into the conventional GFCR system (shown in FIG. 1) utilizing single-element detectors and back-end balancing electronics. Accordingly, FIG. 5 illustrates the incorporation of light producer 140 and controller 142 in a conventional GFCR system (e.g., GFCR system 10 shown in FIG. 1).

Each of GFCR systems 100 and 300 provide an improved target gas detection system suitable for use in many applications where the actual image of the area being evaluated is of little or no interest. Indeed, since defocusing of the image is essential to achieve the elimination of false difference signals due to scene intensity variation, the actual image is not discernable at the image plane of detector arrays 116 and 126. Therefore, for applications requiring the image to be resolved, the GFCR system of the present invention can be further equipped such that the defocus advantage is maintained in a structure that also provides for the reconstruction of the image at the detector arrays.

Figure 6:
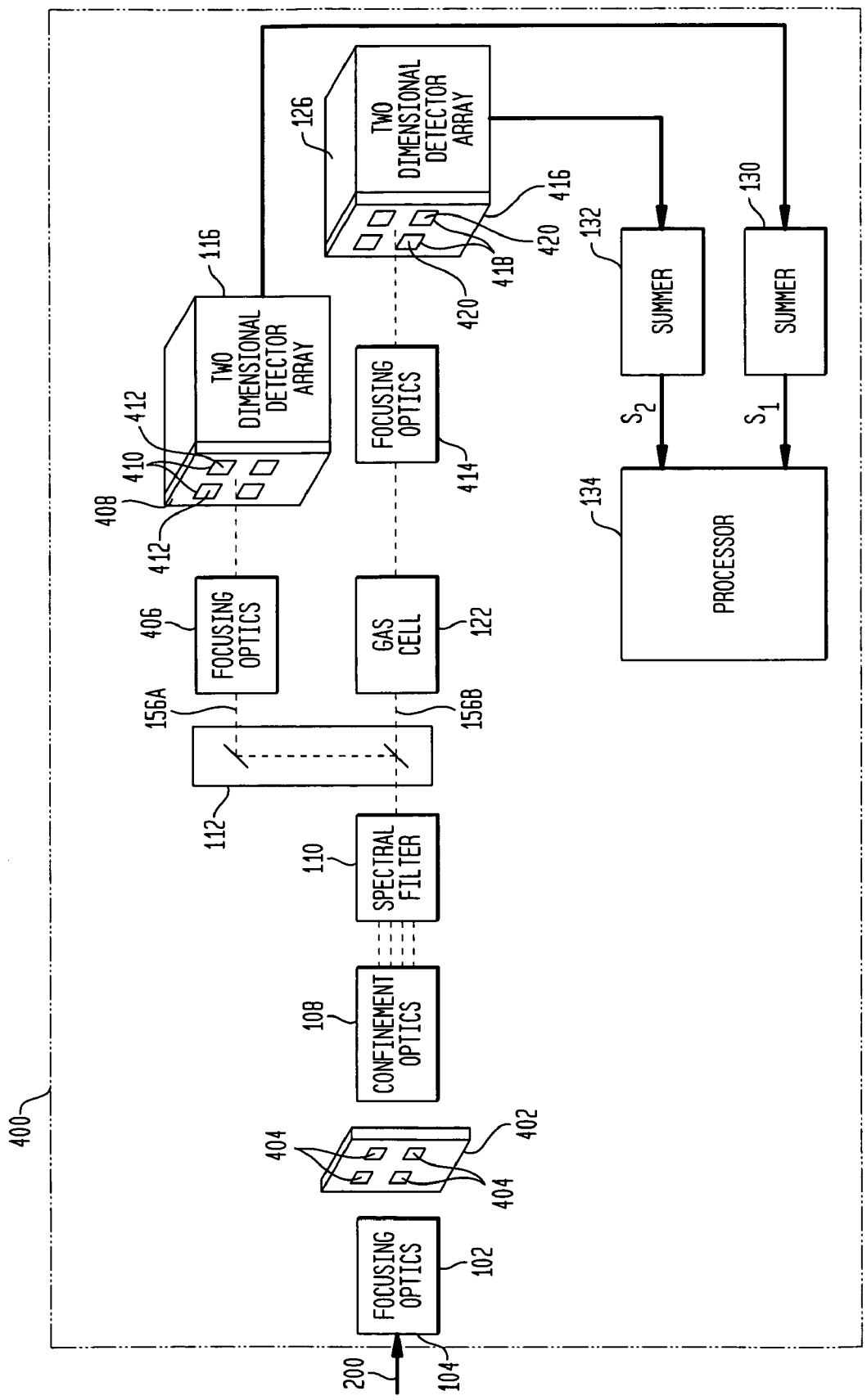
FIG. 6 is a schematic view of the GFCR system in FIG. 2 further equipped with partitioning elements in order to generate an image of the scene being observed by the GFCR system.

The re-imaging features to be described below can be incorporated into either of GFCR systems 100 or 300 without departing from the scope of the present invention. By way of an illustrative example, the re-imaging features of the present invention are illustrated in a GFCR system 400 in FIG. 6 where system 400 is an enhancement of the previously-described GFCR system 100 (FIG. 2).

In general, GFCR system 400 partitions the field-of-view (FOV) at the focal plane of focusing optics 102 into multiple FOV "pieces" which are re-assembled in the same fashion at the image plane of detector arrays 116 and 126. More specifically, a FOV partitioning element 402 is positioned at the focal plane of focusing optics 102. Partitioning element 402 comprises a field stop having an array of apertures 404 formed therethrough that effectively partition the image impinging thereon into a corresponding array of FOV "pieces". The size, number and/or shape of apertures 404 (and the resulting FOV pieces) can be tailored for a specific application and, therefore, are not limitations on the present invention. If the GFCR system is to include the above-described calibration features, partitioning element 402 can be backed with a light-scattering grid element (not shown) with a light source (not shown) being provided at a position that is optically behind the grid element as previously described.

Each resulting FOV "piece" passed by partitioning element 402 is collimated and split into two spatially-separated paths as previously described. In each path, focusing optics are used to re-image the FOV pieces onto another partitioning element that matches partitioning element 402 as will be explained further below. Specifically, in the non-absorbing path, focusing optics 406 is disposed to focus the FOV pieces onto a partitioning element 408 having apertures 410 formed therethrough that are matched to apertures 404. A diffuser 412 is positioned in each of apertures 410. Partitioning element 408 is positioned right at the image plane of detector array 116. In a similar fashion, focusing optics 414 are disposed to focus the FOV pieces onto a partitioning element 416 having apertures 418 formed therethrough that are matched to apertures 404. A diffuser 420 is positioned in each of apertures 418. Partitioning element 416 is positioned right at the image plane of detector array 126.

In operation, rather than defocusing the image onto each detector array, GFCR system 400 re-images the FOV from the collimated light at a partitioning diffuser (i.e., the partitioning and diffusing elements in each path) that "matches" the FOV pieces generated at partitioning element 402. The term "matches" as used herein means that each FOV piece created at partition 402 will pass through a corresponding aperture formed in one of partitioning elements 408 or 416. This insures that light from different FOV pieces will not mix with light from other FOV pieces so that light from each FOV piece impinges on an independent set of light detecting elements of the corresponding detector array.

Scene resolution will be based on the effective resolution of the partitioning elements. The outputs of detector array 116 and 126 can be processed in subsets of pixels corresponding to each area/zone defined by the partitioning elements. For example, each subset of pixels could be summed, differenced, and normalized independently. Thus, this embodiment of the present invention achieves all of the defocus advantages described above while still generating an image of the scene of interest.

Although the invention has been described relative to a specific embodiment thereof, there are numerous variations and modifications that will be readily apparent to those skilled in the art in light of the above teachings. For example, the GFCR system of the present invention could use additional optical elements (e.g., polarizers) that may be required for certain applications, but do not impact the functions of the present invention. Such elements can be included without departing from the scope of the present invention. It is therefore to be understood that, within the scope of the appended claims, the invention may be practiced other than as specifically described.

What is claimed as new and desired to be secured by Letters Patent of the United States is:

1. A gas filter correlation radiometry (GFCR) system, comprising:

an optical train having an entrance aperture, said optical train adapted to receive light from a scene of interest at said entrance aperture, said optical train (i) using the light to form an image of the scene at a focal plane within said optical train, (ii) confining light from a selected field-of-view of the image at said focal plane to a spectral band at which a gas of interest absorbs, and (iii) splitting the confined light into first and second paths;

a region that is substantially non-interfering with respect to said spectral band, said region being disposed along said first path;

a first optical detector defined by a two-dimensional array of optical detection elements disposed in said region;

a first diffuser disposed in said region at a position that is optically in front of said first optical detector, said first diffuser assuring that each portion of the confined light from said selected field-of-view of the image is identically distributed across at least a portion of said optical detection elements of said first optical detector wherein each of said optical detection elements of said first optical detector generates an output signal;

a gas cell filled with the gas of interest, said gas cell disposed along said second path and permitting the confined light from said selected field-of-view of the image to pass therethrough;

a second optical detector defined by a two-dimensional array of optical detection elements;

a second diffuser disposed at a position that is optically between said gas cell and said second optical detector, said second diffuser assuring that each portion of the confined light from said selected field-of-view of the image is identically distributed across at least a portion of said optical detection elements of said second optical detector wherein each of said optical detection elements of said second optical detector generates an output signal; and processing means coupled to said first and second optical detectors for (i) summing said output signals generated by said first optical detector to form a first sum, (ii) summing said output signals generated by said second optical detector to form a second sum, (iii) generating a difference between said first and second sums, and (iv) normalizing said difference using at least one of said first and second sums.

2. A GFCR system as in claim 1 wherein said region is evacuated.

3. A GFCR system as in claim 1 wherein said region contains a gaseous media.

4. A GFCR system as in claim 1 wherein said region contains a solid media.

5. A GFCR system as in claim 1 wherein said first diffuser images said entrance aperture at a plane aligned with said optical detection elements of said first optical detector.

6. A GFCR system as in claim 1 wherein said second diffuser images said entrance aperture at a plane aligned with said optical detection elements of said second optical detector.

7. A GFCR system as in claim 1 further comprising means for selectively producing a calibrating light from within said optical train at said focal plane.

8. A GFCR system as in claim 7 wherein said means periodically turns said calibrating light on and off.

9. A gas filter correlation radiometry (GFCR) system, comprising:

focusing optics having an entrance aperture through which light from a a scene of interest passes, said focusing optics focusing the light onto a focal plane to form an image;

a field stop positioned at said focal plane for permitting light from a selected field-of-view of the image so-focused to pass therethrough;

collimating optics disposed to receive the image so-passed through said field stop and to collimate light indicative of the image so-received;

a spectral filter disposed to receive the light so-collimated and pass a spectral band thereof at which a gas of interest absorbs;

beam splitting optics disposed to receive said spectral band of the light so-passed and split same into first and second paths;

a region that is substantially non-interfering with respect to said spectral band, said region being disposed along said first path;

a first optical detector defined by a two-dimensional array of optical detection elements disposed in said region;

a first diffuser disposed in said region at a position that is optically in front of said first optical detector, said first diffuser assuring that each portion of the light from said selected field-of-view of the image is identically distributed across at least a portion of said optical detection elements of said first optical detector wherein each of said optical detection elements of said first optical detector generates an output signal;

a gas cell filled with the gas of interest, said gas cell disposed along said second path and permitting the light so-collimated to pass therethrough;

a second optical detector defined by a two-dimensional array of optical detection elements;

a second diffuser disposed at a position that is optically between said gas cell and said second optical detector, said second diffuser assuring that each portion of the light from said selected field-of-view of the image is identically distributed across at least a portion of said optical detection elements of said second optical detector wherein each of said optical detection elements of said second optical detector generates an output signal; and processing means coupled to said first and second optical detectors for (i) summing said output signals generated by said first optical detector to form a first sum, (ii) summing said output signals generated by said second optical detector to form a second sum, and (iii) generating a measure of the gas of interest present in the scene of interest using said first and second sums.

10. A GFCR system as in claim 9 wherein said region is evacuated.

11. A GFCR system as in claim 9 wherein said region contains a gaseous media.

12. A GFCR system as in claim 9 wherein said region contains a solid media.

13. A GFCR system as in claim 9 wherein said first diffuser images said entrance aperture at a plane aligned with said optical detection elements of said first optical detector.

14. A GFCR system as in claim 9 wherein said second diffuser images said entrance aperture at a plane aligned with said optical detection elements of said second optical detector.

15. A GFCR system as in claim 9 wherein said processing means generates said measure by generating a difference between said first and second sums, and normalizing said difference using at least one of said first and second sums.

16. A GFCR system as in claim 9 further comprising means for selectively producing a calibrating light at said focal plane.

17. A GFCR system as in claim 16 wherein said means periodically turns said calibrating light on and off.

* * * * *